(12) United States Patent
Lin et al.

(10) Patent No.: US 9,931,348 B2
(45) Date of Patent: Apr. 3, 2018

(54) VANADIUM COMPOUNDS AS THERAPEUTIC ADJUNCTS FOR CARTILAGE INJURY AND REPAIR

(75) Inventors: Sheldon S. Lin, Chatham, NJ (US); David N. Paglia, New Britain, CT (US); James P. O'Connor, Fanwood, NJ (US); Aaron Wey, East Brunswick, NJ (US); Joseph Benevenia, Montclair, NJ (US); Virak Tan, Short Hill, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/130,830

(22) PCT Filed: Jul. 6, 2012

(86) PCT No.: PCT/US2012/045771
§ 371 (c)(1),
(2), (4) Date: Jul. 2, 2014

(87) PCT Pub. No.: WO2013/006798
PCT Pub. Date: Jan. 10, 2013

(65) Prior Publication Data
US 2015/0030653 A1 Jan. 29, 2015

Related U.S. Application Data

(60) Provisional application No. 61/504,777, filed on Jul. 6, 2011.

(51) Int. Cl.
| | | |
|---|---|---|
| *A61K 31/555* | (2006.01) | |
| *A61K 33/24* | (2006.01) | |
| *A61K 45/06* | (2006.01) | |
| *A61L 31/08* | (2006.01) | |
| *A61L 31/16* | (2006.01) | |

(52) U.S. Cl.
CPC ............ *A61K 31/555* (2013.01); *A61K 33/24* (2013.01); *A61K 45/06* (2013.01); *A61L 31/08* (2013.01); *A61L 31/16* (2013.01); *A61L 2300/224* (2013.01); *A61L 2420/04* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 3,915,151 A | 10/1975 | Kraus | |
| 4,878,915 A | 11/1989 | Brantigan | |
| 5,614,206 A | 3/1997 | Randolph et al. | |
| 5,842,477 A * | 12/1998 | Naughton et al. | ............ 128/898 |
| 5,871,779 A * | 2/1999 | Cruz | .............. 424/646 |
| 6,569,204 B1 | 5/2003 | Aldecoa | |
| 6,743,786 B2 * | 6/2004 | Uckun | ..................... C07F 9/005 514/184 |
| 8,936,804 B2 | 1/2015 | Lin et al. | |
| 9,144,633 B2 | 9/2015 | Lin et al. | |
| 2001/0014662 A1 | 8/2001 | Rueger et al. | |
| 2004/0002558 A1 | 1/2004 | McKay | |
| 2004/0014727 A1 | 1/2004 | Garrett | |
| 2004/0121025 A1 | 6/2004 | McKee | |
| 2004/0230309 A1 | 11/2004 | DiMauro et al. | |
| 2005/0079200 A1 | 4/2005 | Rathenow et al. | |
| 2005/0201987 A1 | 9/2005 | Pirhonen et al. | |
| 2006/0036253 A1 | 2/2006 | Leroux et al. | |
| 2007/0073385 A1 | 3/2007 | Schaeffer et al. | |
| 2007/0196642 A1 | 8/2007 | Feldstein et al. | |
| 2008/0031917 A1 | 2/2008 | Miller et al. | |
| 2008/0069852 A1 | 3/2008 | Shimp et al. | |
| 2009/0068285 A1 | 3/2009 | LeGeros et al. | |
| 2009/0214468 A1 | 8/2009 | Lin et al. | |
| 2009/0220566 A1 | 9/2009 | Barralet et al. | |
| 2009/0226534 A1 | 9/2009 | Marchosky | |
| 2009/0298777 A1 | 12/2009 | McKay | |
| 2013/0171094 A1 | 7/2013 | Lin et al. | |
| 2014/0044768 A1 | 2/2014 | Lin et al. | |

FOREIGN PATENT DOCUMENTS

| | | |
|---|---|---|
| CN | 1511595 A | 7/2004 |
| CN | 100344334 C | 10/2007 |
| FR | 2842750 A1 | 1/2004 |
| JP | 03-120257 | 5/1991 |
| JP | 05-140200 | 6/1993 |
| JP | 08-034744 | 2/1996 |
| JP | 2002-138042 A | 5/2002 |
| JP | 2002542802 A | 12/2002 |

(Continued)

OTHER PUBLICATIONS

Kato, Yukio, The Journal of Cell Biology, vol. 104 (1987), pp. 311-319.*
Hayao, Ide et al., "Vanadium Promotes Osteogenesis," Health Chemistry, Department of Medicine, Toho University, Omori Medical Center, Toho University [date unknown, cited in office action for Japanese App. 212-549109 on Dec. 25, 2014] (Abstract).
Makinen, Marvin et al., "Metabolism and Bioenergetics: Structural Origins of the Insulin-mimetic Activity of Bis (acetylacetonato)oxoyanadium(IV)" J. Biol. Chem., 2002, vol. 277, pp. 12215-12220.
Zhang, Shuang-Qing et al., "Effects on the Bones of Vanadyl Acetylacetonate by Oral Administration: A Comparison Study in Diabetic Rats," J. Bone Miner Metab, (2007), vol. 25, Issue 5, pp. 293-301.

(Continued)

*Primary Examiner* — Dennis J Parad
*Assistant Examiner* — Lyndsey Beckhardt
(74) *Attorney, Agent, or Firm* — Fox Rothschild LLP (57) ABSTRACT

A method for repairing an injury of cartilage in a patient by local administration of an organovanadium agent or use of an implantable device for delivery of an organovanadium agent. Implantable devices containing an organovanadium agent and methods of making these implantable devices are also disclosed.

17 Claims, 2 Drawing Sheets

(56) References Cited

FOREIGN PATENT DOCUMENTS

| JP | 2007529515 A | 10/2007 |
|---|---|---|
| JP | 2011512957 A | 4/2011 |
| RU | 2105529 | 2/1998 |
| WO | 96/36333 A1 | 11/1996 |
| WO | 00/24730 A1 | 5/2000 |
| WO | 20050032466 A2 | 4/2005 |
| WO | 2007090433 A2 | 8/2007 |
| WO | 2008048647 A1 | 4/2008 |
| WO | 20090068285 A1 | 6/2009 |
| WO | 2009/111300 | 9/2009 |
| WO | 20100114827 A1 | 10/2010 |
| WO | 2011/088318 | 7/2011 |
| WO | 2011/0088318 A1 | 7/2011 |
| WO | 2012/079024 A2 | 6/2012 |
| WO | 2013082295 A1 | 6/2013 |

OTHER PUBLICATIONS

Information about Related Patents and Patent Applications, see section 6 of the accompanying Information Disclosure Statement Letter, which concerns Related Patents and Patent Applications.
Hamrin et al., "Local effect of vanadate on interstitial glucose and lactate concentrations in human skeletal muscle," Life Sciences (2005), vol. 76, pp. 2329-2338.
Ide et al., "Vanadium promotes osteogenesis" Convention Program Summary of the Japanese Society for Bone and Mineral Research, (2004), vol. 22, p. 171 (Abstract only).
Kishimoto, "Why are not increase of bone density and effect of fracture prevention consistent?" Journal of Osteoporotic Medicine (2005), vol. 4, No. 3, pp. 44-48 (Abstract only).
Barrio et al.: "Vanadium and Bone Development: Putative Signaling Pathways", Jul. 2006, Canada Journal of Physiology and Pharmacology, vol. 84, No. 7, pp. 677-686.
Cortizo et al: "Osteogenic Activity of Vanadyl(IV)-Ascorbate Complex: Evaluation of its Mechanism of Action", The International Journal of Biochemistry & Cell Biology, 2006, vol. 38, pp. 1171-11180.
Kazuyuki, et al.: "In Vitro Prominent Bone Regeneration by Release Zinc Ion from Zn-Modified Implant", Biochemical and Biophysical Research Communications, Jul. 2011 (Jul. 28, 2011), vol. 412, No. 2, 28 , pp. 273-278.
Wang, et al.: "Zinc-Containing Apatite Layers on External Fixation Rods Promoting Cell Activity", ACTA Biomaterialia, Elsevier, Amsterdam, Mar. 1, 2010, vol. 6, No. 3, pp. 962-968.
Baquer, et al: "Metabolic and Molecular Action of Trigonella Foenum-Graecum (Fenugreek) and Trace Metals in Experimental Diabetic Tissues", J. Biosci., Jun. 2011, pp. 383-396.
Adachi, et al.: "Comparative Study of Insulin-Mimetic Activity of Vanadium and Zinc Complexes", Biomed Res. Trace Elements, 2004, vol. 15, No. 4, pp. 351-354.
Yoshikawa, et al: "Challenge of Studies on the Development of New Zn Complexes (Zn(opt)2) to Treat Diabetes Mellitus", Metallomics, 2011, vol. 3, pp. 686-692.
Baquer, et al. "Regulation of Glucose Utilization and Lipogenesis in Adipose Tissue of Diabetic and Fat Fed Animals: Effects of Insulin and Manganese", J. Biosci., Mar. 2003, vol. 28, No. 2, pp. 215-221.
Subasinghe, et al.: "The Insulin-Mimetic Action of Mn2+: Involvement of Cyclic Nucleotides and Insulin in the Regulation of Hepatic Hexokinase and Glucokinase", Biochemical Medicine, 1985, vol. 34, pp. 83-92.
Slappey, et al: "Guidelines to Decortication in Posterolateral Spine Fusion", Apr. 1998, J. Spinal Disord., vol. 11, No. 2. (Abstract only).
USC Center for Spinal Surgery; "Anterior Lumbar Corpectomy and Fusion & Anterior Thoracic Corpectomy and Fusion", Mar. 20, 2007 Retrieved from the Internet: <URL:http://www.uscspine,com/treatment/corpectomy-fusion.cfm>.
USC Center for Spinal Surgery; " Posterior Lumbar Fusion (PLF)", Mar. 20, 2007. Retrieved from the Internet: <URL:http://www.uscspine.com/treatment/posterior-lumbar-fusion.cfm>.
Columbia University Medical Center; "Lumbar Fusion and Fixation", Nov. 14, 2010. Retrieved from the Internet <URL:http;//www.columbianeurosurgery.org/specialties/spine/procedures/surgical/lumbar-fusion-and-fixation>.
Raggatt, et al: "Cellular and Molecular Mechanisms of Bone Remodeling", Journal of Biological Chemistry, Aug. 13, 2010, vol. 285, No. 33, pp. 25103-25108.
Kalfas, Iain H.: "Principles of Bone Healing", Neurosurg Focus, Apr. 2001, vol. 10, No. 4, pp. 1-4.
Navarro, et al: "Biomaterials in Orthopaedics", J. R. Soc. interface, Jul. 30, 2008, vol. 5, pp. 1137-1158.

\* cited by examiner

VANADIUM COMPOUNDS AS THERAPEUTIC ADJUNCTS FOR CARTILAGE INJURY AND REPAIR

CROSS-REFERENCE TO RELATED APPLICATIONS

This application is the U.S. National Phase of international Patent Application Serial No. PCT/US12/45771, filed Jul. 6, 2012, which claims priority under 35 § 119(e) to U.S. Provisional Patent Application Ser. No. 61/504,777, filed on Jul. 6, 2011, both of which are hereby incorporated by reference in their entireties.

FIELD OF THE INVENTION

The present invention relates to compositions or devices comprising organovanadium compounds as therapeutic adjuncts for cartilage regeneration and repair.

BACKGROUND OF THE INVENTION

Articular cartilage has little capacity to repair itself or regenerate intrinsically. Therefore, cartilage defects repair by forming scar tissue (or fibrocartilage) from the subchondral bone. This scar tissue is deficient in type II collagen and has "abnormal" proteoglycans (which have inferior biomechanical characteristics) and lower load bearing capacity, and its formation will often result in short term recovery only. This later surface deterioration may progress to give chronic pain and poor function and may in some cases lead to early onset osteoarthritis.

A regional database study of over 30,000 patients found that 63% of knees that undergo arthroscopy are found to have disease in the articular cartilage, and articular chondral lesions are suspected to be the cause of as many as 10% of all knee hemarthroses. Trauma is the most common etiology, but other conditions, such as osteochondritis dissecans and chondromalacia patellae (abnormal softening of the patellar articular cartilage), are also accepted as causes of symptomatic painful articular lesions. Isolated articular cartilage injuries secondary to trauma are rare; more often articular cartilage injuries are seen with other traumatic injuries to the knee, such as ligamentous or meniscal damage.

Osteochondral lesions (and osteochondritis dessicans) are common in adolescents. A recent magnetic resonance imaging study found that after acute trauma the most common injuries to the immature knee were chondral in nature. Traumatic forces are transmitted through the subchondral bone beneath the cartilage, resulting in an osteochondral fracture. Treatment of larger and symptomatic lesions is often surgical. Ideally the aim of surgery is to provide an environment that allows whatever repair tissue is produced (preferably hyaline cartilage) to be integrated with native healthy tissue to provide long term durability and a "normal" knee joint.

In recent years, the potential use of organovanadium as an alternative or adjunct treatment for diabetes has been examined. However, the effects of vanadium compounds on cartilage healing and regeneration are unknown. In particular, no evaluation of vanadium therapy on cartilage regeneration, in particular, repairing of cartilage injuries, has been performed, and in vivo data on cartilage regeneration or repair in the presence of vanadium are still unavailable.

SUMMARY OF THE INVENTION

The present invention provides a novel method for accelerating cartilage healing or repair using organovanadium agents. The present invention thus obviates the need for developing specialized methods to deliver growth factors and thereby reduces costs associated with therapy, eliminates specialized storage and enhances ease of use.

In one aspect the present invention provides a method for repairing an injury of cartilage in a patient in need thereof by locally administering a therapeutically effective amount of an organovanadium compound to the patient.

In another aspect the present invention provides a method for repairing an injury of cartilage in a patient in need thereof by treating the patient with an implantable device having a composite surface coating containing an organovanadium compound.

In another aspect the present invention provides an implantable device for implant in a cartilage to treat an injury of the cartilage, containing an organovanadium compound.

In another aspect the present invention provides use of an organovanadium compound or composition thereof for manufacture of a medicament or device for repairing a cartilage injury.

The therapeutic adjunct of the present invention may find application in, e.g., traumatic cartilaginous injuries, osteochondral lesions, osteochondral fracture, osteochondritis dissecans, chondromalacia, and avascular necrosis. Application of the present invention as therapeutic cartilaginous adjunct will also enhance the currently utilized surgical techniques.

The present invention may find wide application in veterinary medicines to treat a variety of factures in a mammalian animal, including but not limited to, horses, dogs, cats, or any other domestic or wild mammalian animals. A particular useful application may be found, for example, in treating an injured race horse. Other aspects and embodiments of the present invention will be further illustrated in the following description and examples.

DETAILED DESCRIPTION OF THE INVENTION

The present invention incorporates the discovery that vanadium-containing agents play a critical role in cartilage repairing and regeneration. In one aspect the present invention provides a method for repairing an injury of a cartilage in a patient in need thereof, by locally administering a therapeutically effective amount of an organo-vanadium compound to a patient.

In one embodiment of this aspect, the organovanadium compound is selected from vanadyl acetylacetonate (VAC), vanadyl sulfate (VS), vanadyl 3-ethylacetylacetonate (VET), and bis(maltolato)oxovanadium (BMOV), and the like.

In a preferred embodiment of this aspect, the organovanadium compound is vanadyl acetylacetonate (VAC).

In another embodiment of this aspect, the cartilage injury is selected from traumatic cartilaginous injuries, osteochondral lesions, osteochondral fracture, osteochondritis dissecans, chondromalacia, avascular necrosis, chemical induced cartilage damage (e.g., steroid injection), and genetic cartilage deficiency, or the like.

In another embodiment of this aspect, the cartilage is an articular cartilage.

In another embodiment of this aspect, the method is used in conjunction with arthroscopic debridement, marrow stimulating techniques, autologous chondrocyte transfers, and autologous chondrocyte implantation, and allografts.

In another embodiment of this aspect, the method is used in conjunction with administration of a cytototoxic agent, cytokine or growth inhibitory agent.

In another embodiment of the present invention, the method is used in conjunction with an allograft/autograft or orthopedic biocomposite.

In another embodiment of this aspect, the patient is a mammalian animal.

In another embodiment of this aspect, the patient is a human.

In another embodiment of this aspect, the patient is a non-diabetic human.

In another embodiment of this aspect, the patient is a horse or dog.

In another preferred embodiment of this aspect, the present invention is particularly suitable for, but is not limited to, repairing cartilage tissue damages that are caused by long term or sudden trauma or injury.

In another aspect the present invention provides a method for repairing an injury of a cartilage in a patient in need thereof comprising treating said patient with an implantable device comprising an organovanadium compound. The implantable device can be a delivery system of a composition containing the organovanadium compound, a vanadium-coated orthopedic implant, or an article that also provides support to an injured or damaged joint.

Organovanadium compounds suitable for use in the present invention include vanadyl acetylacetonate (VAC), vanadyl sulfate (VS), vanadyl 3-ethyl-acetylacetonate (VET), bis(maltolato)oxovanadium (BMOV), and the like. In a preferred embodiment of this aspect, the organovanadium compound is vanadyl acetylacetonate (VAC).

In another embodiment of this aspect, the cartilage injury is selected from traumatic cartilaginous injuries, osteochondral lesions, osteochondral fracture, osteochondritis dissecans, chondromalacia, avascular necrosis, chemical induced cartilage damage (e.g., steroid injection), and genetic cartilage deficiency, or the like.

In another embodiment of this aspect, the cartilage injury is that of an articular cartilage.

In another embodiment of this aspect, the method is used in conjunction with arthroscopic debridement, marrow stimulating techniques, autologous chondrocyte transfers, and autologous chondrocyte implantation, and allografts.

In another embodiment of this aspect, the method is used in conjunction with administration of a cytototoxic agent, cytokine or growth inhibitory agent.

In another embodiment of this aspect, the method is used in conjunction with an allograft/autograft or orthopedic biocomposite.

In another embodiment of this aspect, the patient is a mammalian animal.

In another embodiment of this aspect, the patient is a human.

In another embodiment of this aspect, the patient is a non-diabetic human.

In another embodiment of this aspect, the patient is a horse or dog.

In another preferred embodiment of this aspect, the present invention is particularly suitable for, but is not limited to, repairing cartilage tissue damages that are caused by long term or sudden trauma, injury and/or diseases.

In another aspect the present invention provides an implantable device for implant in cartilage tissue to treat an injury of the cartilage containing an organovanadium compound. In one embodiment of this aspect, the organovanadium compound is selected from vanadyl acetylacetonate (VAC), vanadyl sulfate (VS), vanadyl 3-ethylacetylacetonate (VET), bis(maltolato)oxovanadium (BMOV), and the like. In a preferred embodiment of this aspect, the organovanadium compound is vanadyl acetylacetonate (VAC).

In another preferred embodiment of this aspect, the device is coated by a composite surface coating containing an organovanadium compound. In another preferred embodiment of this aspect, the organovanadium compound in the composite surface coating is vanadyl acetylacetonate.

In another embodiment of this aspect, the present invention is particularly suitable for, but is not limited to, repairing cartilage tissue damages that are caused by long term or sudden trauma or injury.

Another aspect of the present invention provides the use of an organovanadium compound or composition thereof for the manufacture of a medicament or device for treatment of a cartilage injury, in particular, without limitations, cartilage tissue damages that are caused by long term or sudden trauma or injury.

In a preferred embodiment of this aspect, the organovanadium compound is selected from vanadyl acetylacetonate (VAC), vanadyl sulfate (VS), vanadyl 3-ethylacetylacetonate (VET) and bis(maltolato) oxovanadium (BMOV).

In a more preferred embodiment of this aspect, the organovanadium compound is vanadyl acetylacetonate (VAC).

In one embodiment, the organovanadium compound of the present invention is an insulin-mimetic.

Preferred sites of interest in the patient include sites in need of cartilage healing and areas adjacent and/or contiguous to these sites. Local administration of an organovanadium can be carried out by any means known to a person of ordinary skill in the art.

The term "therapeutically effective amount," as used herein, means an amount at which the administration of an agent is physiologically significant. The administration of an agent is physiologically significant if its presence results in a detectable change in the bone healing process of the patient.

It will be appreciated that actual preferred amounts of a pharmaceutical composition used in a given therapy will vary depending upon the particular form being utilized, the particular compositions formulated, the mode of application, and the particular site of administration, and other such factors that are recognized by those skilled in the art including the attendant physician or veterinarian. Optimal administration rates for a given protocol of administration can be readily determined by those skilled in the art using conventional dosage determination tests.

Dosages of a vanadium compound employable with the present invention may vary depending on the particular use envisioned. The determination of the appropriate dosage or route of administration is well within the skill of an ordinary physician.

For example, when in vivo administration of a vanadium compound is employed, normal dosage amounts may vary from about 10 ng/kg up to about 100 mg/kg of mammal body weight or more per day, preferably about 1 g/kg/day to 10 mg/kg/day, depending upon the route of administration. Guidance as to particular dosages and methods of delivery is provided in the literature; see, for example, U.S. Pat. Nos. 4,657,760; 5,206,344; 5,225,212; 5,871,799; and 6,232,340. It is anticipated that different formulations will be effective for different treatments and different disorders, and that administration intended to treat a specific bone site or condition, may necessitate delivery in a manner different from that for another site or condition.

The formulations used herein may also contain more than one active compound as necessary for the particular indication being treated, preferably those with complementary activities that do not adversely affect each other. Alternatively, or in addition, the formulation may comprise a cytotoxic agent, cytokine or growth inhibitory agent. Such molecules are present in combinations and amounts that are effective for the intended purpose.

Therapeutic formulations of vanadium compounds in the vanadium delivery systems employable in the methods of the present invention are prepared for storage by mixing the vanadium compound having the desired degree of purity with optional pharmaceutically acceptable carriers, excipients, or stabilizers (Remington's Pharmaceutical Sciences 16th edition, Osol, A. Ed. (1980)). Such therapeutic formulations can be in the form of lyophilized formulations or aqueous solutions. Acceptable biocompatible carriers, excipients, or stabilizers are nontoxic to recipients at the dosages and concentrations employed, and may include buffers, for example, phosphate, citrate, and other organic acids; antioxidants including ascorbic acid and methionine; preservatives (e.g. octadecyldimethylbenzyl ammonium chloride; hexamethonium chloride; benzalkonium chloride, benzethonium chloride; phenol, butyl or benzyl alcohol; alkyl parabens, for example, methyl or propyl paraben; catechol; resorcinol; cyclohexanol; 3-pentanol; and m-cresol); low molecular weight (less than about 10 residues) polypeptides; proteins, for example, serum albumin, gelatin, or immunoglobulins; hydrophilic polymers, for example, polyvinylpyrrolidone; amino acids, for example, glycine, glutamine, asparagine, histidine, arginine, or lysine; monosaccharides, disaccharides, and other carbohydrates including glucose, mannose, dextrins, or hyaluronan; chelating agents, for example, EDTA; sugars, for example, sucrose, mannitol, trehalose or sorbitol; salt-forming counter-ions, for example, sodium; metal complexes (e.g. Zn-protein complexes); and/or non-ionic surfactants, for example, TWEEN™, PLURONICS™ or polyethylene glycol (PEG).

In order for the formulations to be used for in vivo administration, they must be sterile. The formulation may be readily rendered sterile by filtration through sterile filtration membranes, prior to or following lyophilization and reconstitution. The therapeutic formulations herein preferably are placed into a container having a sterile access port, for example, an intravenous solution bag or vial having a stopper pierceable by a hypodermic injection needle.

The formulations used herein may also contain more than one active compound as necessary for the particular indication being treated, preferably those with complementary activities that do not adversely affect each other. Alternatively, or in addition, the formulation may comprise a cytotoxic agent, cytokine or growth inhibitory agent. Such molecules are present in combinations and amounts that are effective for the intended purpose.

The vanadium may also be entrapped in microcapsules prepared, for example by coacervation techniques or by interfacial polymerization, for example, hydroxy-methylcellulose or gelatin-microcapsules and poly-(methylmethacrylate) microcapsules, respectively. Such preparations can be administered in colloidal drug delivery systems (for example, liposomes, albumin microspheres, microemulsions, nano-particles and nanocapsules) or in macroemulsions. Such techniques are disclosed in Remington's Pharmaceutical Sciences, 16th Edition (or newer), Osol A. ed. (1980).

Optionally, the organovanadium agent in the vanadium delivery systems includes a porous calcium phosphate, non-porous calcium phosphate, hydroxy-apatite, tricalcium phosphate, tetracalcium phosphate, calcium sulfate, calcium minerals obtained from natural bone, inorganic bone, organic bone, or a combination thereof.

Where sustained-release or extended-release administration of vanadium in the vanadium delivery systems is desired, microencapsulation is contemplated. Microencapsulation of recombinant proteins for sustained release has been successfully performed with human growth hormone (rhGH), interferon-$\alpha$, -$\beta$, -$\gamma$ (rhIFN-$\alpha$, -$\beta$, -$\gamma$), interleukin-2, and MN rgp120. Johnson et al., Nat. Med. 2: 795-799 (1996); Yasuda, Biomed. Ther. 27: 1221-1223 (1993); Hora et al., Bio/Technology 8: 755-758 (1990); Cleland, "Design and Production of Single Immunization Vaccines Using Polylactide Polyglycolide Microsphere Systems" in Vaccine Design: The Subunit and Adjuvant Approach, Powell and Newman, eds., (Plenum Press: New York, 1995), pp. 439-462; WO 97/03692, WO 96/40072, WO 96/07399 and U.S. Pat. No. 5,654,010.

Suitable examples of sustained-release preparations include semipermeable matrices of solid hydrophobic polymers containing the vanadium in the vanadium delivery systems, which matrices are in the form of shaped articles, e.g. films, or microcapsules. Examples of sustained-release matrices include one or more polyanhydrides (e.g., U.S. Pat. Nos. 4,891,225; 4,767,628), polyesters, for example, polyglycolides, polylactides and polylactide-co-glycolides (e.g., U.S. Pat. No. 3,773,919; U.S. Pat. No. 4,767,628; U.S. Pat. No. 4,530,840; Kulkarni et al., Arch. Surg. 93: 839 (1966)), polyamino acids, for example, polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly(vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and .gamma.-ethyl-L-glutamate, non-degradable ethylene-vinyl acetate, degradable lactic acid-glycolic acid copolymers, for example, the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained-release formulations may be composed of degradable biological materials, for example, bioerodible fatty acids (e.g., palmitic acid, steric acid, oleic acid, and the like). Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957,744; Valle et al., Polym. Mater. Sci. Eng. 62: 731-735 (1991). HA polymer grafted with polyethylene glycol has also been prepared as an improved delivery matrix which reduced both undesired drug leakage and the denaturing associated with long term storage at physiological conditions. Kazuteru, M., J. Controlled Release 59:77-86 (1999). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and non-toxic polyurethanes, polyhydroxylbutyrates, polyhydroxyvalerates, polyalkylene oxalates, polyalkylene succinates, poly(malic acid), chitin, and chitosan.

Alternatively, biodegradable hydrogels may be used as controlled-release materials for the vanadium compounds in the vanadium delivery systems. Through the appropriate choice of macromers, membranes can be produced with a range of permeability, pore sizes and degradation rates suitable for different types of vanadium compounds in the vanadium delivery systems.

Alternatively, sustained-release delivery systems for vanadium in the vanadium delivery systems can be composed of dispersions. Dispersions may further be classified as either suspensions or emulsions. In the context of delivery vehicles for a vanadium compound, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with a vanadium compound in the present invention include multiple emulsions, microemulsions, microdroplets and liposomes. Microdroplets are unilamellar phospholipid vesicles that consist of a spherical lipid layer with an oil phase inside. E.g., U.S. Pat. No. 4,622,219 and U.S. Pat. No. 4,725,442. Liposomes are phospholipid vesicles prepared by mixing water-insoluble polar lipids with an aqueous solution.

Alternatively, the sustained-release formulations of vanadium in the vanadium delivery systems may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in Biogradable Polymers as Drug Delivery Systems M. Chasin and R. Langeer, editors (Marcel Dekker: New York, 1990), pp. 1-41.

The route of administration of "local vanadium" via a "delivery system" is in accordance with known methods, e.g. via immediate-release, controlled-release, sustained-release, and extended-release means. Preferred modes of administration for the organovanadium delivery system include injection directly into afflicted site and areas adjacent and/or contiguous to these site or surgical implantation of the organovanadium delivery system directly into afflicted sites and area adjacent and/or contiguous to these sites. This type of system may allow temporal control of release as well as location of release as stated above.

As an illustrated example, Vanadium may be continuously administered locally to a site via a delivery pump. In one embodiment, the pump is worn externally (in a pocket or on the belt) and attached to the body with a long, thin, and flexible plastic tubing that has a needle or soft cannula (thin plastic tube), and the cannula or needle is inserted and then left in place beneath the skin. The needle or cannula and tubing can be changed, for example, every 48 to 72 hours. The pump would store the vanadium in a cartridge and release it based on the optimal delivery rate. Optionally, the pump is programmed to give a small dose of a drug continuously through the day and night, which in certain circumstances may be preferred.

When an implantable device coated by a composite surface coating comprising an organovanadium compound is used, the coating can be formed by any methods known in the relevant art, for example, without limitation, those disclosed in Petrova, R. and Suwattananont, N., J. Electr. Mat., 34(5):8 (2005)). For example, suitable methods include chemical vapor deposition (CVD), physical vapor deposition (PVD), thermochemical treatment, oxidation, and plasma spraying (Fischer, R. C., Met. Progr. (1986); Habig, K. H., Tribol. Int., 22:65 (1989)). A suitable coating of the present invention may also comprise combinations of multiple, preferably two or three, layers obtained by forming first boron diffusion coating followed by CVD (Zakhariev, Z., et al., Surf Coating Technol., 31:265 (1987)). Thermochemical treatment techniques have been well investigated and used widely in the industry. This is a method by which nonmetals or metals are penetrated by thermodiffusion followed by chemical reaction into the surface. By thermochemical treatment, the surface layer changes its composition, structure, and properties.

Other suitable coating techniques may include, but are not limited to, carburizing, nitriding, carbonitriding, chromizing, and aluminizing. Among these coating techniques, boronizing, being a thermochemical process, is used to produce hard and wear-resistant surfaces. As a person of ordinary skill in the art would understand, different coating techniques may be used to make the vanadium-based coatings and coated devices of the present invention in order to have desired properties suitable for specific purposes.

EXAMPLES

Materials and Methods

I. The BB Wistar Rat Model
Animal Source and Origin

Diabetic Resistance (DR) BB Wistar rats used in the study were obtained from a breeding colony at UMDNJ-New Jersey Medical School (NJMS). The rats were housed under controlled environmental conditions and fed ad libitum. All research protocols were approved by the Institutional Animal Care and Use Committee at University of Medicine and Dentistry of New Jersey—New Jersey Medical School.

Diabetic Resistant BB Wistar Rats

A total of 62 DR BB Wistar rats were utilized in the study. Due to inappropriate fracture configuration, six samples were removed. The remaining 56 animals were used for early histology and immunohistochemistry, distributed amongst the control saline (n=26), and 1.5 mg/kg VAC treated (n=30) groups.

Closed Femoral Fracture Model

Surgery was performed in DR animals between ages 85 and 110 days, using a closed mid-diaphyseal fracture model, on the right femur as described previously (Beam, H. A., et al., *J. Orthop. Res.,* 20(6):1210-1216 (2002); Gandhi, A., et al., *Bone.,* 38(4):540-546 (2006)).

Figure 1:
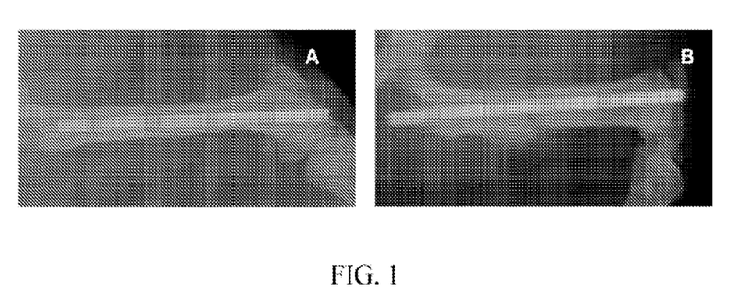
FIG. 1 represents post-operative X-ray photographs taken immediately post-operative. (A) Einhorn model, (B) model used in this work. (Note in (B) the Kirschner wire is going through the trochanter, this helps to stabilize the fracture site and prevent the migration of the Kirschner wire).

General anesthesia was administrated by intraperitoneal (IP) injection of ketamine (60 mg/kg) and xylazine (8 mg/Kg). The right leg of each rat was shaved and the incision site was cleansed with Betadine and 70% alcohol. An approximately 1 cm medial, parapatellar skin incision was made over the patella. The patella was dislocated laterally and the interchondylar notch of the distal femur was exposed. An entry hole was made with an 18 gauge needle and the femur was reamed with the 18 gauge needle. A Kirschner wire (316 LVM stainless steel, 0.04 inch diameter, Small Parts, Inc., Miami Lakes, Fla.) which underwent thermochemical pack boriding was inserted the length of the medullary canal, and drilled through the trochanter of the femur. The kirschner wire was cut flush with the femoral condyles. After irrigation, the wound was closed with 4-0 vicryl resorbable suture. A closed midshaft fracture was then created unilaterally with the use of a three-point bending fracture machine. X-rays were taken to determine whether the fracture is of acceptable configuration. An appropriate fracture is an approximately mid-diaphyseal, low energy, transverse fracture (FIG. 1). The rats were allowed to ambulate freely immediately post-fracture. This closed fracture model is commonly used to evaluate the efficacy of osseous wound healing devices and drugs.

Experimental Treatments

Early Histology

The fractured femora were resected at 7 days post-fracture, decalcified, dehydrated, embedded in paraffin, and sectioned using standard histological techniques (Beam, H. A., et al., *J. Orthop. Res.,* 20(6):1210-1216 (2002); Gandhi, A., et al., *Bone,* 37(4):482-490 (2005)). Sections were stained with Masson's Trichrome (Accustain™ Trichrome Staining kit, Sigma Diagnostics, St. Louis, Mo.) for histological observation using an Olympus BH2-RFCA microscope (Olympus Optical Co., Ltd., Shinjuku-ku, Tokyo, Japan). Digital images were collected using a Nikon DXM1200F digital camera (Nikon, Tokyo, Japan). Cartilage, new bone, and total callus area were measured from the digital images using Image-Pro Plus software (version 5, Media Cybernetics, Inc., Silver Spring, Md.). Total cartilage and new bone area were normalized to total callus area and expressed as the percent area. Limitations of this procedure include inconsistencies in histomorphometric evaluation between reviewers.

To examine the effects of VAC at later stages of fracture healing, femora were resected from animals in the groups described above at day 10, embedded and sectioned using standard histological techniques. This includes dehydration, soaking in Xylenes 1-3, and finally pre-embedding in a layer of Polymethylmethacrylate (PMMA). After embedding in pure PMMA and allowed to solidify in a hot water bath, slides were sectioned from the PMMA blocks, polished, and stained with a combination of Stevenel's blue and Van Gieson picro-fuchsin (SVG). Histological images of fracture calluses were obtained using an Olympus SZX12 upright microscope (Olympus Optical Co, LTD, Japan) connected via a CCD camera (Optronics, Goleta, Calif.) to a personal computer and analyzed with the Bioquant software package (Biometrics, Inc, Nashville, Tenn.). Parameters that were compared include a) callus area, b) percent calcified tissue area, and c) percent cartilage area. Limitations of this procedure include production of slides with high thicknesses, due to the difficulties associated with sectioning PMMA. This limits the number of possible sections that may be cut for staining in addition to analysis of cellular morphology, due to overlapping layers of cells. Possible inconsistencies in histomorphometry between reviewers is a further limitation of late histomorphometry.

Early Immunohistochemistry

At days 2, 4, and 7, and 10, animals were injected intraperitoneally with 30 mg/kg of 5-bromo-2' deoxyuridine (BrdU, Sigma Chemical Co., St. Louis, Mo.) one hour prior to sacrifice to label replicating cells as a measure of cellular proliferation. The fractured femurs were resected and fixed in formalin, decalcified (Immunocal, Decal Corp., Tallman, N.Y.), embedded in paraffin, and sectioned longitudinally (5 μm thick). Cells positive for BrdU incorporation were detected by immunohistochemistry using commercially available reagents (DAKO Corp., Carpentaria, Calif.). Digital images of each fracture were collected with an Olympus BH2-RFCA microscope equipped with a Nikon DXM1200f camera. For each specimen, callus area was measured and the BrdU positive cells in the periosteal callus region were counted using Image Pro Plus software. All BrdU positive cells in the external callus to a maximum of 1 cm proximal and distal of the fracture site and 3 mm from the external surface of the femur were counted. The number of BrdU positive cells was normalized per unit area of callus and only one datum per rat (BrdU positive cells per $mm^2$) was used for the statistical analysis (Tyndall, W. A., et al., *Clin. Orthop.,* 408:319-330 (2003)). The disadvantage of using BrdU is that the user risks exposing himself/herself to this carcinogenic substance. BrdU labeling is considered the gold standard for labeling of proliferating cells.

Data and Statistical Analysis

A student t-test was performed to determine differences (SigmaStat 3.0, SPSS Inc., Chicago, Ill.). A P value less than 0.05 was considered statistically significant.

Results

General Health

The age and percent weight change following surgery to the day of sacrifice was comparable among all groups. There were no statistical differences found.

Histology Results

In animals treated with VAC, histomorphometric analysis revealed a statistically higher ($p<0.05$) percent cartilage in animals treated with 1.5 mg/kg VAC, compared to both 7 and 10 days (Tables 1 and 2). At 7 and 10 days post fracture local VAC treatment lead to 200% and 88% more cartilage respectively, compared to untreated (saline) controls. Values of % cartilage were normalized to the total callus area.

TABLE 1

Early Histomorphometric Analysis of Vanadium Effects

|  | 7 Days Post-Fracture | | |
|---|---|---|---|
|  | % Cartilage Subperiosteal Region | % Cartilage Gap Region | % Cartilage Normalized to Total Callus Area |
| Saline Control | 2.0 ± 1.1 (n = 6) | 6.0 ± 4.0 (n = 6) | 3.0 ± 1.7 (n = 6) |
| 1.5 mg/kg Local VAC | 5.0 ± 1.8* (n = 6) | 13.0 ± 4.2* (n = 6) | 9.0 ± 2.5* (n = 6) |

The data represent mean values (±S.D.).
*Represent values statistically higher than control, $p < 0.05$ versus control.

TABLE 2

Late Histomorphometric Analysis of Vanadium Effects

|  | 10 Days Post-Fracture | |
|---|---|---|
|  | Callus Area (mm$^2$) | % Cartilage Normalized to Total Callus |
| Saline Control | 15.8 ± 2.3 (n = 5) | 16.3 ± 2.8 (n = 5) |
| 1.5 mg/kg Local VAC | 18.4 ± 3.6 (n = 7) | 30.6 ± 12.4* (n = 7) |

The data represent mean values (±S.D.).
*Represent values statistically higher than control, $p < 0.05$ versus control.

Immunohistochemistry Results

In animals treated with VAC, there were no significant differences in cell proliferation at 2, or 4 days post-fracture, but there were significantly more proliferating cells per unit area (p<0.05) in the subperiosteal at 7, and 10 days post-fracture (Table 3.3). At 7, and 10 days post fracture local VAC treatment lead to increases of 62% and 84% more BRDU+cells per square millimeter respectively, compared to untreated (saline) controls.

TABLE 3

Early Cell Proliferation (BRDU) Analysis of Vanadium Effects

|  |  | Control | 1.5 mg/kg Local VAC |
|---|---|---|---|
| 2 Days Post-Fracture | Positive Proliferating Cells per unit Subperiosteal Region Area (cells/mm$^2$) | 312 ± 56 (n = 5) | 405 ± 145 (n = 5) |
|  | Positive Proliferating Cells per unit Gap Region Area (cells/mm$^2$) | 270 ± 104 (n = 5) | 283 ± 96 (n = 5) |
| 4 Days Post-Fracture | Positive Proliferating Cells per unit Subperiosteal Region Area (cells/mm$^2$) | 479 ± 221 (n = 5) | 311 ± 146 (n = 5) |
|  | Positive Proliferating Cells per unit Gap Region Area (cells/mm$^2$) | 347 ± 245 (n = 5) | 391 ± 219 (n = 5) |
| 7 Days Post-Fracture | Positive Proliferating Cells per unit Subperiosteal Region Area (cells/mm$^2$) | 53 ± 24 (n = 6) | 86 ± 11* (n = 6) |
|  | Positive Proliferating Cells per unit Gap Region Area (cells/mm$^2$) | 64 ± 20 (n = 6) | 84 ± 25 (n = 6) |
| 10 Days Post-Fracture | Positive Proliferating Cells per unit Subperiosteal Region Area (cells/mm$^2$) | 34 ± 7 (n = 6) | 66 ± 22* (n = 6) |
|  | Positive Proliferating Cells per unit Gap Region Area (cells/mm$^2$) | 26 ± 10 (n = 6) | 23 ± 15 (n = 6) |

The data represent mean values (±S.D.).
*Represent values statistically higher than control, $p < 0.05$ versus control.

This study has demonstrated that local VAC accelerates the production of cartilage in the healing callus, post-fracture. These data has indicated that local vanadium treatment may be an effective method to regenerate cartilage in non-diabetic fracture patients.

II. The Rabbits Model

A total of 6 New Zealand rabbits, 6 months of age were used in this study. The protocol was approved by the Animal Institutional Care and Use Committee. The animals were housed in the animal facility at NJMS and fed ad libitum.

Surgical Protocol

Prior to surgery each animal was anesthetized with an intramuscular injection of 1 mg/kg acepromazine and 0.01 mg/kg glycopyrolate. After waiting 10-15 minutes, 35 mg/kg ketamine+5 mg/kg xylazine was administered. Ophthalmic ointment was applied to both eyes. 10 mg/kg of enrofloxacin was administered for antibacterial prophylaxis and a 12 mcg/hr fentanyl patch was applied to the backside of the rabbit or to the inside of the rabbit's ears. Anesthesia was administered and maintained by a veterinary tech.

Bilateral hindlimbs were scrubbed with a povidone-iodine solution with sterile drapes placed. Both knees were then arthrotomized using a standard medial parapatellar approach with the patella flipped laterally, exposing both the patellar grove and the medial femoral condyles.

A full-thickness defect with a diameter of 3 mm, depth of 3 mm was created through the articular cartilage/subchondral bone of the patellar groove and the posterior weight-bearing surface of the medial and lateral femoral condyles in rabbits using a drill equipped with a 3-mm diameter drill bit. The depth was calibrated by marking the depth of 3 mm on the drill bit. A 3×3 mm plug of VAC/CaSO$_4$ (1.5 mg/kg VAC) was placed in the defects of 2 animals, a 3×3 mm plug of CaSO$_4$ alone was placed in the defects of two animals as a positive control, and the defects were left empty in the remaining two animals. After completion of the procedure the patella will then be reduced, and the joint capsule repaired with interrupted 3-0 vicryl suture and skin with interrupted 3-0 nylons. The procedure will be replicated in the left hindlimb of all animals.

Postoperatively, the wounds were treated daily with neomycin ointment. In addition, enrofloxacin 5 mg/kg was administered BID for 5 postoperative days. The limbs were not immobilized and the animals were allowed unrestricted movement in their cages immediately after recovery from anesthesia. The rabbits were sacrificed 8 weeks postoperatively with an intravenous injection of Euthasol (1 ml/10 lb).

Histological Assessment

The distal portion of each femur was removed and fixed in 10% buffered formaldehyde and decalcified with 10% EDTA solution. An osteochondral block including the two repaired defects were cut and embedded in paraffin. Five-μm-thick sections were cut in the sagittal plane, mounted on glass slides, and stained with either hematoxylineosin or Safranin O. Sections were examined in a blinded manner and independently scored by two independent, blinded investigators according to the International Cartilage repair society histological grading scale.

A Mann-Whitney Rank Test was performed for analysis of histologic scoring. Statistical analysis was performed using SigmaStat.

Results

Figure 2:
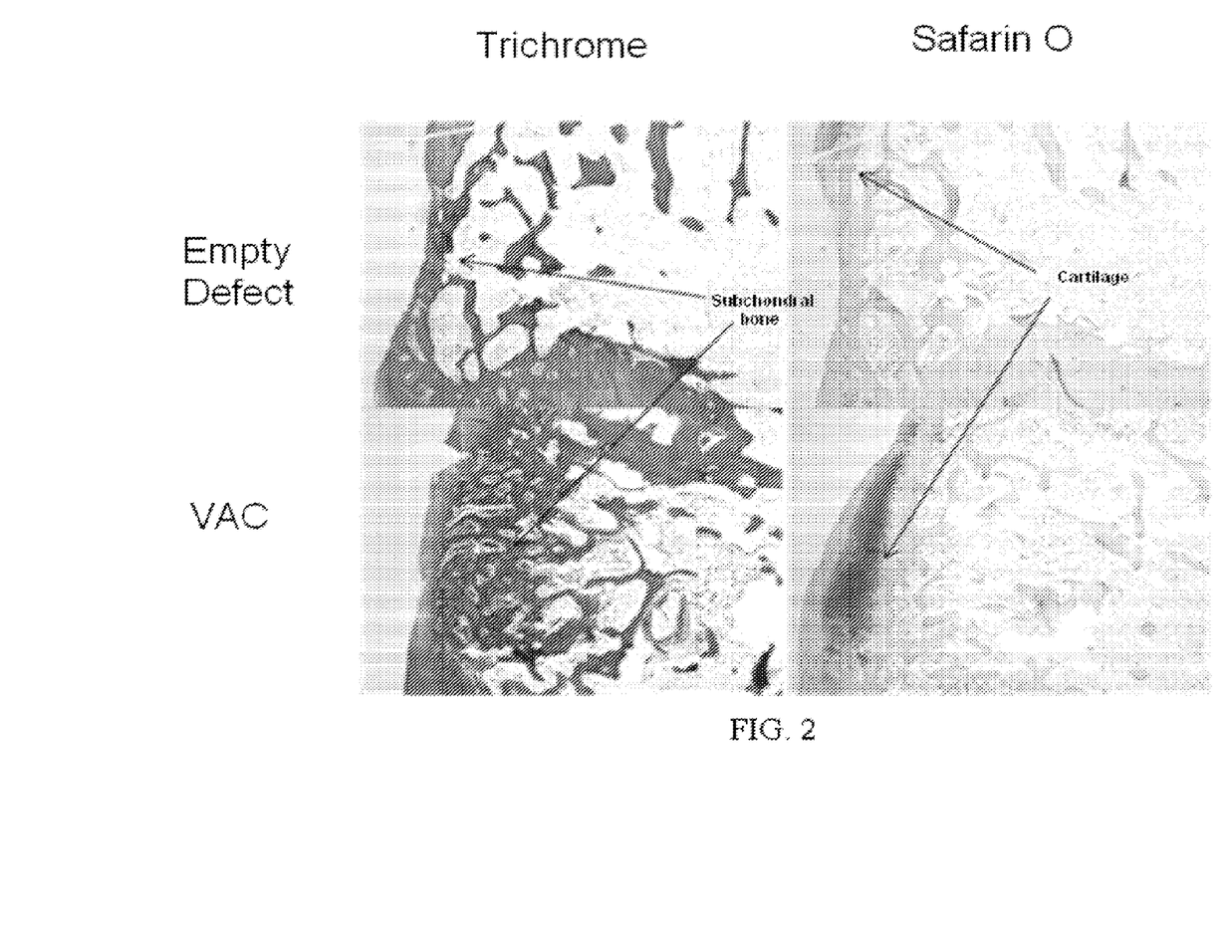
FIG. 2 illustrates representative histological samples comparing empty defect and VAC treated groups. Bone is dark blue on the Trichrome stain, and cartilage is stained red on the Safarin O stain.

With the histologic scoring, the VAC group showed a strong trend toward significance compared to the control (25±9 vs 17±9; p=0.100) and CaSO$_4$ groups (25±9 vs 16±7; p=0.054) (Table 4). In the VAC treated group, three of the six samples regenerated articular cartilage, whereas the control and CaSO$_4$ groups regenerated no cartilage, or formed either fibrocartilage or unorganized cartilage (FIG. 2).

TABLE 4

Macroscopic and histological scoring of osteochondral defects

| | Histologic Scoring |
|---|---|
| Empty Defect (n = 5) | 17 ± 6 |
| CaSO4 (n = 6) | 19 ± 4 |
| VAC (n = 6) | 26 ± 7 |

Discussion

This study demonstrates the potential role of vanadium in the treatment of osteochondral defects in a rabbit model. To our knowledge this is the first study of vanadium on healing of osteochondral lesions.

Multiple studies have explored the effects of local insulin application on bone formation. (See, e.g., Dedania, J., et al., *J. Orthop. Res.*, 29:92-99 (2011)). Stuck found more advanced healing microscopically in a rabbit fibula osteotomy model for animals injected with intravenous insulin. (Stuck, W., *J. Bone Joint Surg. Am.*, 14:109-115 (1932)). This was most notable in animals sacrificed between two and four weeks after surgery. Similar results were demonstrated by Cornish et al. after injecting insulin over the right hemicalvariae of adult mice for five days. (Cornish, J., et al., *Calcif. Tissue Int.*, 59:492-495 (1996)). All indices of bone formation were significantly increased in insulin-treated hemicalvariae compared with the noninjected hemicalvariae. Paglia et al. found that locally delivered Ultralente insulin increased callus mechanical strength in a non-diabetic rat femur fracture model. (Paglia, D., et al., The angiogenic effects of local ultralente insulin on periosteal bone formation. Orthopaedic Research Society 2011 Meeting, Long Beach Calif.) These studies, however, do not address the problem of systemic administration of insulin, or the short half life of insulin when injected locally at the site of interest. To our knowledge, however, no studies have been performed exploring the effects of insulin on osteochondral lesions.

Because insulin without a carrier has a short half-life, the palmitic acid Linplant was proposed as a potential vehicle to deliver insulin at the appropriate site of action for an extended period of time Dedania et al. analyzed the effects of a time released local insulin implant in a rat segmental defect model. (Dedania, J., et al., *J. Orthop. Res.*, 29:92-99 (2011)). Defects treated with the time released insulin implant had significantly more new bone formation and greater quality of bone than those treated with palmitic acid alone seen on histology and histomorphometry. Prior studies by our lab confirms their findings of the potential benefits of a time-released substance using a rat posterolateral transverse process fusion model. Significant differences were found with radiographs, manual palpation, and microCT in the insulin treatment groups versus controls. This study found similar results with insulin-mimetic agents of VAC and zinc.

One potential issue using insulin-mimetics lies in its hypoglycemic action. Systemic blood glucose levels and hypoglycemia are concerning when applying an insulin-mimetic. However, previous studies have demonstrated that a time released insulin implant does not affect the systemic insulin, glucose, or glycosylated hemoglobin values. (Dedania, J., et al., *J. Orthop. Res.*, 29:92-99 (2011); Gandhi, A., et al., *Bone*, 37:482-490 (2005)). Our data supports this with little if any impact upon the systemic glucose values.

This study is the first to examine the effects of vanadium compounds in a rabbit osteochondral defect model. Our results provide strong evidence that local vanadium delivery at the defect improves the healing potential of these defects. The invention may be used as a treatment regimen to increase rates of osteochondral defect healing in patients.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

All references cited hereby are incorporated by reference in their entirety.

What is claimed is:

1. A method for repairing an injury of cartilage tissue in a patient in need thereof, comprising locally administering to the cartilage injury site of said patient a composition sterilized for in vivo cartilage administration consisting of an organovanadium compound in an amount effective to regenerate cartilage, wherein said cartilage injury is selected from the group consisting of traumatic cartilaginous injuries, osteochondral lesions, osteochondral fracture, osteochondritis dissecans, chondromalacia, avascular necrosis, steroid-induced cartilage damage and genetic cartilage deficiency.

2. The method of claim 1, wherein said organovanadium compound is selected from the group consisting of vanadyl acetylacetonate (VAC), vanadyl sulfate (VS), vanadyl 3-ethylacetylacetonate (VET), and bis(maltolato)oxo vanadium (BMOV).

3. The method of claim 1, wherein said organovanadium compound is vanadyl acetylacetonate (VAC).

4. The method according to claim 1, wherein said cartilage is an articular cartilage.

5. The method according to claim 1, wherein the method is used in combination with arthroscopic debridement, marrow stimulating techniques, autologous chondrocyte transfers, and autologous chondrocyte implantation, and allografts.

6. The method according to claim 1, wherein the method is used in conjunction with administration of a cytotoxic agent, cytokine or growth inhibitory agent.

7. The method according to claim 1, wherein the method is used in conjunction with an allograft, autograft or orthopedic biocomposite.

8. The method according to claim 1, wherein said patient is a mammalian animal.

9. A method for repairing an injury of a cartilage in a patient in need thereof, comprising applying to the site of said injury an implantable device coated with a composition sterilized for in vivo cartilage administration in an amount effective to regenerate cartilage and consisting of an organovanadium compound.

10. The method of claim 9, wherein said organovanadium compound is selected from the group consisting of vanadyl acetylactenoate (VAC), vanadyl sulfate (VS), vanadyl 3-ethylacetylacetonate (VET), and bis(maltolato) oxo-vanadium (BMOV).

11. The method of claim 9, wherein said organovanadium compound is vanadyl acetylacetonate (VAC).

12. The method according to claim 9, wherein said cartilage injury is selected from the group consisting of traumatic cartilaginous injuries, osteochondral lesions, osteochondral fracture, osteochondritis dissecans, chondromalacia, avascular necrosis, chemical induced cartilage damage, and genetic cartilage deficiency.

13. The method according to claim 9, wherein said cartilage injury is that of an articular cartilage.

14. The method according to claim 9, wherein the method is used in conjunction with arthroscopic debridement, marrow stimulating techniques, autologous chondrocyte transfers, and autologous chondrocyte implantation, and allografts.

15. The method according to claim 9, wherein the method is used in conjunction with administration of a cytotoxic agent, cytokine or growth inhibitory agent.

16. The method according to claim 9, wherein the method is used in conjunction with an allograft, autograft or orthopedic biocomposite.

17. The method according to claim 9, wherein said patient is a mammalian animal.

\* \* \* \* \*